US00PP31088P2

(12) United States Plant Patent
Head

(10) Patent No.: US PP31,088 P2
(45) Date of Patent: Nov. 19, 2019

(54) GARDENIA PLANT NAMED 'WAH-SG'

(50) Latin Name: *Gardenia jasminoides*
Varietal Denomination: WAH-SG

(71) Applicant: Southern Plant Group, LLC, Marietta, GA (US)

(72) Inventor: William A. Head, Walhalla, SC (US)

(73) Assignee: SOUTHERN PLANT GROUP, LLC, Marietta, GA (US)

( * ) Notice: Subject to any disclaimer, the term of this patent is extended or adjusted under 35 U.S.C. 154(b) by 0 days.

(21) Appl. No.: 16/350,615

(22) Filed: Dec. 11, 2018

(51) Int. Cl.
*A01H 5/02* (2018.01)
*A01H 6/76* (2018.01)

(52) U.S. Cl.
USPC ..... Plt./255

(58) Field of Classification Search
USPC ..... Plt./266, 255
See application file for complete search history.

*Primary Examiner* — Susan McCormick Ewoldt
*Assistant Examiner* — Karen M Redden
(74) *Attorney, Agent, or Firm* — Buchanan Ingersoll & Rooney PC

(57) ABSTRACT

A new and distinct variety of *Gardenia* plant, referred to by its cultivar name, 'WAH-SG', is provided which forms single, small sized, fragrant, white colored inflorescences. Attractive, glossy, dark green colored foliage is formed, which contrasts beautifully with the blossoms. The vegetation is moderately vigorous and the growth habit is tight, compact, and rounded. The new variety is well suited for proving attractive ornamentation in the landscape.

2 Drawing Sheets

Figure 1:
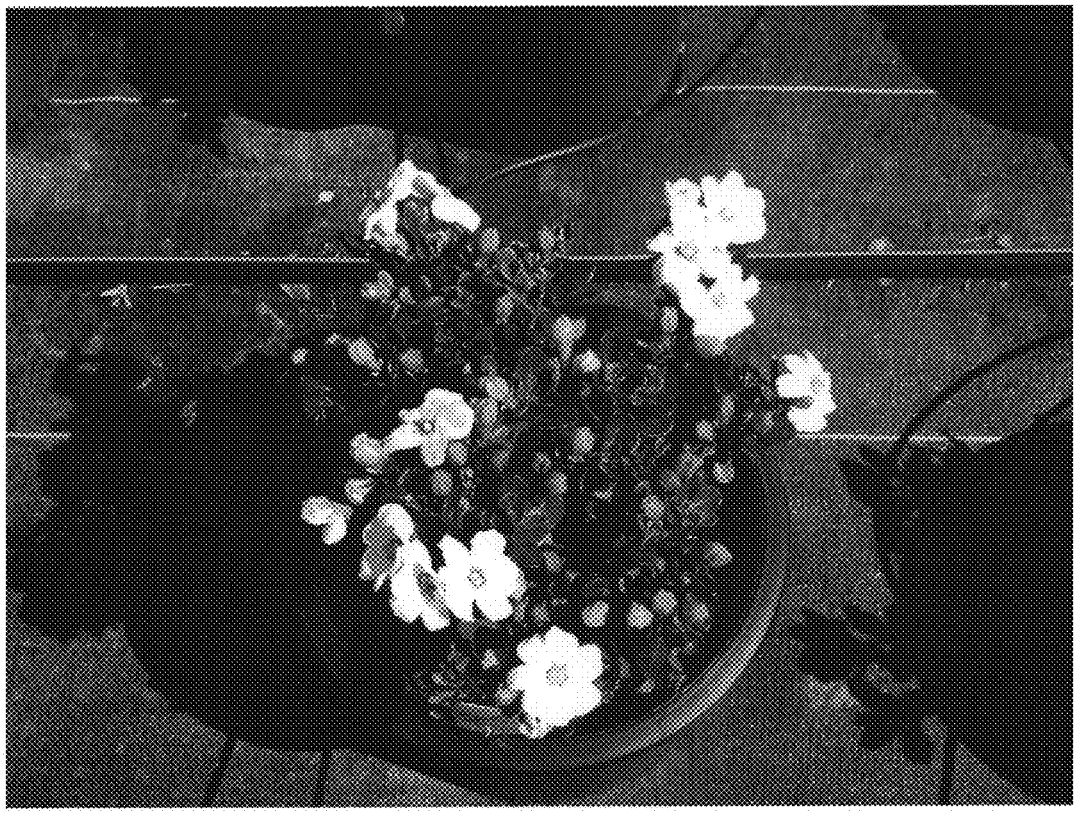

Botanical/commercial classification:
Latin name—*Gardenia jasminoides.*
Common name—*Gardenia* Plant.
Varietal denomination—'WAH-SG'.

SUMMARY OF THE INVENTION

The new variety of *Gardenia jasminoides Gardenia* plant was created in a controlled breeding program during the spring of 2006 at Seneca, S.C., U.S.A., by open pollination in the hope that they would contribute the desired characteristics. The female parent (i.e., the seed parent) was the 'Daisy' variety (non-patented). The male parent (i.e., the pollen parent) is unknown.

The parentage of the new variety can be summarized as follows:

'Daisy' x unknown

The new cultivar was discovered and selected as a single flowering plant within the progeny of the above-stated open-pollination during the summer of 2008 in a controlled environment at Seneca, S.C. Selective study resulted in the identification of a single plant of the new variety.

It was found that the new variety of *Gardenia* plant of the present invention possesses the following combination of characteristics:

(a) forms attractive, fragrant, small-sized single, white-colored inflorescences,
(b) exhibits glossy, dark green colored foliage; and
(c) provides moderately vigorous vegetation, with tight, compact, and rounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Daisy' variety (i.e., the seed parent) displays upright to mounded growth habit, whereas the new variety exhibits tight, compact, and rounded growth habit. Moreover, the new variety can be readily distinguished from other similar non-parental varieties. For example, the 'Kleim's Hardy' variety (not patented) displays larger flower size, provides a less compact growth habit, and exhibits larger leaves that are spaced farther apart compared to the new variety.

The new variety has been found to undergo asexual propagation at Seneca, S.C., Hickory, N.C., and El Campo, Tex. by softwood cuttings since the summer of 2010. Asexual propagation by softwood cuttings in Seneca, S.C., Hickory, N.C., and El Campo, Tex. has shown that the characteristics of the new variety are stable and are strictly transmissible by such asexual propagation from one generation to another. Accordingly, the new variety undergoes asexual propagation in a true-to-type manner.

The new variety has been named 'WAH-SG'.

BRIEF DESCRIPTION OF THE PHOTOGRAPHS

The accompanying photographs shows as nearly true as it is reasonably possible to make the same, in color illustrations of this character, typical specimens of the new variety. The *Gardenia* plants of the new variety were approximately one year of age and were observed while growing outdoors at Cochranville, Pa., U.S.A. in 3-gallon containers.

FIG. 1—illustrates a specimen the plant—canopy view of the overall growth and flowering habit.

Figure 2:
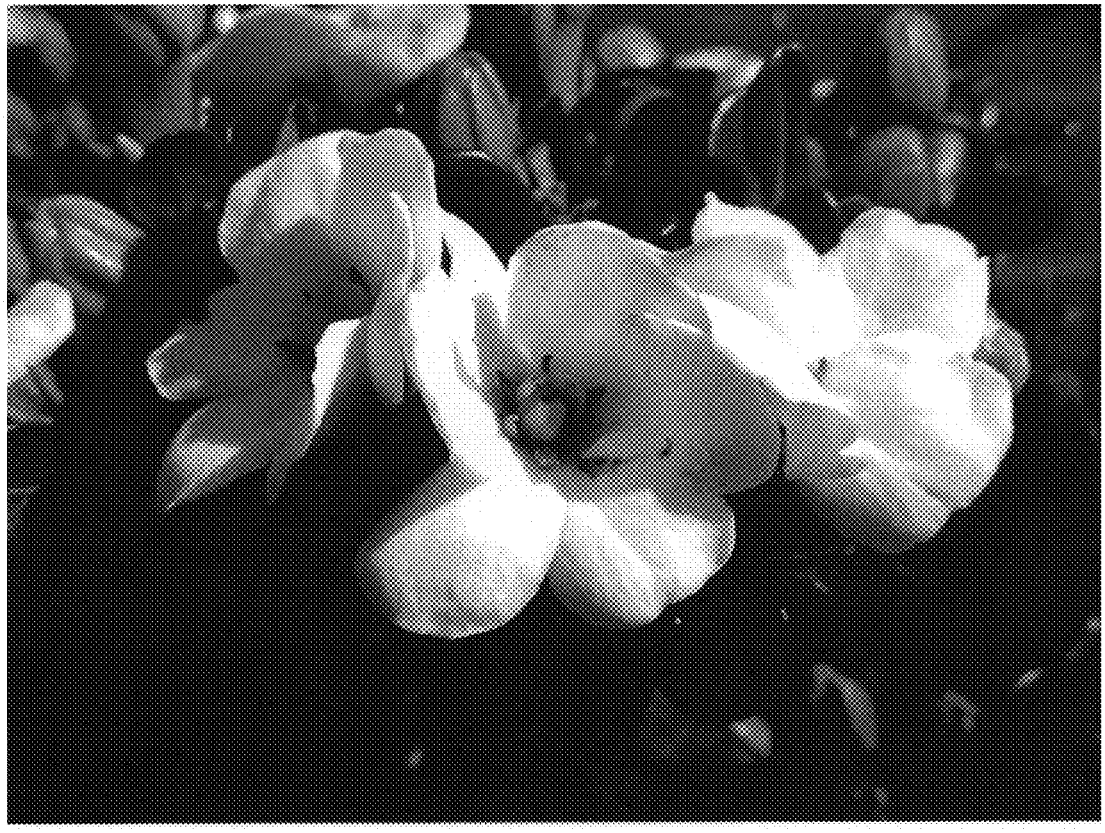

FIG. 2—illustrates specimens of open flowers.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The color values were determined in June 2019 under natural light conditions in Cochranville, Pa. Measurements and numerical values represent averages of typical plants.

Class: *Gardenia* Plant.

Plant:

*Habit*.—Tight, compact, and rounded.

*General appearance*.—Moderately vigorous.

*Size*.—Height from soil level to top of plant plane is approximately 31.0 cm on average and width is approximately 33.0 cm on average.

*Branching habit*.—Freely branching and pinching enhances branching. Quantity of lateral branches per plant: approximately 7 main branches.

*Branch*.—Strength: strong. Length: approximately 15.0 cm on average. Diameter: approximately 6.0 mm on average. Length of central internode: approximately 1.5 cm on average. Texture: furfuraceous to scurfy. Color of mature stems: commonly near Brown Group N200A.

Foliage:

*Fragrance*.—None detected.

*Form*.—Simple.

*Arrangement*.—Opposite.

*Leaves*.—Shape: rounded. Margin: entire. Apex: rounded. Base: cuneate. Venation pattern: pinnate. Length of mature leaf: Approximately 2.5 cm on average. Width of mature leaf: approximately 2.0 cm on average. Texture of upper and lower surfaces: Glabrous, with very glossy upper surface. Color of upper surface of young foliage: commonly near Green Group 137A with venation of near Green Group 137B. Color of lower surface of young foliage: commonly near Green Group 137C with venation of near Green Group 137B. Color of upper surface of mature foliage: commonly near Green Group 139A with venation of near Green Group 139B. Color of lower surface of mature foliage: commonly near Green Group 139B with venation of near Green Group 139C.

*Petiole*.—Length: approximately 2.0 mm on average. Diameter: approximately 1.0 mm on average. Texture: Glabrous. Color: commonly near Yellow-Green Group 146B.

Inflorescence:

*Flower general description*.—Type: single. Quantity per plant: approximately 30 open at a time. Fragrance: strong, pleasantly sweet. Aspect: upward to outward.

*Bud just before opening*.—Shape: oblong. Length: approximately 3.5 cm on average. Diameter: approximately 1.2 cm on average. Color: commonly near Yellow-Green Group N144B.

*Corolla*.—Shape: rotate. Depth: approximately 3.5 cm on average. Diameter: approximately 5.0 cm on average.

*Petals*.—Quantity: 6. Shape: obovate. Margin: entire. Apex: rounded. Base: truncate. Length: approximately 2.0 cm on average. Width: approximately 1.7 cm on average. Texture of upper and lower surfaces: glabrous. Color of upper and lower surfaces when fully open: commonly near White Group NN155B.

*Calyx*.—Shape: star-shaped. Depth: approximately 1.0 cm on average. Diameter: approximately 8.0 mm on average.

*Sepals*.—Quantity: 6. Shape: narrow lanceolate. Margin: entire. Apex: acute. Base: fused. Length: approximately 1.0 cm on average. Width: approximately 2.0 mm on average. Texture of upper surface: glabrous. Texture of lower surface: glabrous. Color of upper and lower surfaces: commonly near Yellow-Green Group 144A.

*Peduncle*.—Strength: strong. Shape: rounded. Aspect: erect to about 30° from branch axis. Length: approximately 1.0 cm on average. Diameter: approximately 3.0 mm on average. Texture: furfuraceous. Color: commonly near Grey-Brown Group N199A.

*Reproductive organs*.—Androecium: Stamen quantity per flower is approximately 6 and stamen length is approximately 7.0 mm on average. Anther shape is narrow oblong, dorsifixed; anther length is approximately 7.0 mm on average; and anther color is commonly near Greyed-Yellow Group 161A. Pollen amount is moderate; pollen color is commonly near Yellow Group 3B. Gynoecium: Pistil quantity is 1 per flower irregularly divided into two or three segments and pistil length approximately 3.5 cm on average. Stigma shape is irregularly elliptic; stigma color is commonly near Yellow Group 7B. Style length is approximately 2.2 cm on average; style color is commonly near Yellow Group 4D. Ovary length is approximately 3.0 mm on average; and ovary color is commonly near Green-White Group 157A.

Development:

*Vegetation*.—Moderately vigorous.

*Commercial crop time*.—Approximately one year from a rooted cutting to finish in a 3-gallon container.

*Hardiness*.—USDA Zone 7 (0° F. to 10° F.).

*Flowering season*.—Flowers in spring with intermittent flowering through fall.

*Lastingness of individual inflorescence on the plant*.—Approximately one week.

*Disease and pest resistance*.—Resistance to pathogens and pests common to *Gardenia* has not been observed.

*Seed and fruit production*.—Neither seed nor fruit production has been observed.

The new 'WAH-SG' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Gardenia* plant characterized by the following combination of characteristics:

(a) forms attractive, fragrant, small-sized single, white-colored inflorescences, (b) exhibits glossy, dark green colored foliage; and (c) provides moderately vigorous vegetation, with tight, compact, and rounded growth habit;

substantially as herein shown and described.

* * * * *